(12) United States Patent
Brookins

(10) Patent No.: US 12,178,745 B1
(45) Date of Patent: Dec. 31, 2024

(54) WEARABLE DEVICE FOR TREATMENTS TO ENHANCE CIRCULATION IN LOWER TORSO

(71) Applicant: Keith Donald Brookins, Miami, FL (US)

(72) Inventor: Keith Donald Brookins, Miami, FL (US)

( * ) Notice: Subject to any disclaimer, the term of this patent is extended or adjusted under 35 U.S.C. 154(b) by 0 days.

(21) Appl. No.: 18/509,556

(22) Filed: Nov. 15, 2023

(51) Int. Cl.
*A61F 7/02* (2006.01)
*A61F 7/00* (2006.01)

(52) U.S. Cl.
CPC ........ *A61F 7/02* (2013.01); *A61F 2007/0022* (2013.01); *A61F 2007/0023* (2013.01); *A61F 2007/0027* (2013.01); *A61F 2007/0092* (2013.01); *A61F 2007/0228* (2013.01); *A61F 2007/0236* (2013.01); *A61F 2007/0257* (2013.01); *A61F 2007/0277* (2013.01)

(58) Field of Classification Search
CPC ................ A61F 7/02; A61F 2007/0022; A61F 2007/0027; A61F 2007/0092; A61F 2007/0228; A61F 2007/0236; A61F 2007/0257; A61F 2007/0277
See application file for complete search history.

(56) References Cited

U.S. PATENT DOCUMENTS

| | | | | |
|---|---|---|---|---|
| 1,477,187 A | * | 12/1923 | Rayne | A61F 5/40 602/73 |
| 2006/0101558 A1 | * | 5/2006 | Coleman | A61F 13/84 2/400 |
| 2010/0094386 A1 | * | 4/2010 | Margolis | A61F 7/00 607/108 |
| 2011/0046703 A1 | * | 2/2011 | Chen | A61F 7/007 607/108 |
| 2013/0338742 A1 | * | 12/2013 | Gallen | A61F 7/02 607/108 |
| 2015/0342326 A1 | * | 12/2015 | Drysdale | A61F 7/02 224/148.5 |

* cited by examiner

*Primary Examiner* — Tigist S Demie
(74) *Attorney, Agent, or Firm* — ALBERT BORDAS P.A.

(57) ABSTRACT

A wearable device for treatments to enhance circulation in a lower torso. The device has a pouch assembly and a strap assembly with a waist belt and lateral straps. The strap assembly is secured around a body. The lateral straps, waist belt, and body create semi-sealed interfaces, forming a functional pocket between the pouch assembly and the body. The pouch assembly can be worn on the front or back of the body. The pouch assembly captures and retains fluids against the body, and allows physical access to the treatment area. With a continuous source of water, the semi-sealed nature of the pouch allows for water to circulate the treatment area. The materials are resistant to temperature, water, suds, human biowaste, and pharmaceutical solutions. The design's practicality and effectiveness in improving lower torso circulation are underscored by the strap assembly's secure fit and standing treatment orientation.

8 Claims, 5 Drawing Sheets

WEARABLE DEVICE FOR TREATMENTS TO ENHANCE CIRCULATION IN LOWER TORSO

BACKGROUND OF THE INVENTION

The present invention relates to wearable medical devices, and more particularly, to wearable medical devices that allow the circulation of fluid around the lower torso to enhance blood circulation, promoting faster healing, cleaning and treatment.

PRIOR ART

Applicant is not aware of any prior art that has the novelties of the present invention.

SUMMARY OF THE INVENTION

The present invention is a unisex wearable device for treatments to enhance circulation in lower torso. This device comprises a pouch assembly and a strap assembly, wherein the pouch assembly contains multiple layers. The pouch assembly comprises a first layer and a second layer, creating a cavity that is semi-sealed. The strap assembly comprises a waist belt, adjustable buckle, lateral straps, adjustable clips and clip snaps. The strap assembly secures the pouch assembly to a body.

The strap assembly is welded to the pouch assembly in two locations. The shorter distance between the belt welds causes the pouch assembly to bow outwards defining the radius of the pouch assembly. Each waist belt end is fitted with an adjustable buckle that, together, secure the pouch assembly to the body. The attachment process involves wrapping the waist belt around the body, the two lateral straps loop under the user's perineal region and one lateral strap attaches to one side of the adjustable buckle and the other lateral strap attaches to the opposite side of the adjustable buckle. The lateral straps are attached to the waist belt by adjustable clips. The device is secured to the user by attaching and adjusting the strap assembly. The device is put on and off using the buckle once adjustments are made.

The pouch assembly has a lower corner. The lower corner has a lateral strap weld. The lateral straps are both welded to the lateral strap weld. The end of each lateral strap is fitted with an adjustable clip. The lateral strap is perforated to allow the adjustable clips to adjust to different sizes by passing under the user's torso. The lateral strap then passes to the other side and up to attach to the adjustable clip. Each adjustable clip attaches to the waist belt and can be further adjusted by sliding the adjustable clips along the waist belt to accommodate comfort and function. This configuration creates a semi-sealed interface between the pouch assembly, waist belt, lateral straps, and the body, forming a pocket. This arrangement allows for the strap assembly to be adapted to many sizes and body types.

The waist belt and lateral straps ensure a snug fit when secured around the body, especially when in a standing position. Both the strap assembly and the pouch assembly are constructed from soft, weldable, and durable materials. The pouch assembly takes on a shape that traps fluids against the body.

The materials used in the strap assembly and pouch assembly are resistant to various elements such as temperature, water, human suds, biowaste, and pharmaceutical solutions. This design ensures the device's longevity and usability in various conditions. The strap assembly is designed to provide secure fastening when the user is standing, contributing to its practicality and effectiveness in improving circulation in the lower torso while standing under a water source that provides a constant source of warm water that is easily regulated.

It is therefore one of the main objects of the present invention to provide a wearable device for treatments to enhance circulation in lower torso that enhances the comfort of patients.

It is another object of this invention to provide a wearable device for treatments to enhance circulation in lower torso that improves the health benefits of patients.

It is another object of this invention to provide a wearable device for treatments to enhance circulation in lower torso that allows reduced recovery times.

It is another object of this invention to provide a wearable device for treatments to enhance circulation in lower torso that allows a steadily replaced water source that is constantly replacing soiled water, cleaning, and it provides a steady temperature due to the constant water exchange.

It is another object of this invention to provide a wearable device for treatments to enhance circulation in lower torso that can be used while standing to further reduce recovery period by discouraging sedentary behavior.

It is another object of this invention to provide a wearable device for treatments to enhance circulation in lower torso that is durable yet cheap to manufacture.

It is another object of this invention to provide a wearable device for treatments to enhance circulation in lower torso that is lightweight and easy to transport.

Further objects of the invention will be brought out in the following part of the specification, wherein detailed description is for the purpose of fully disclosing the invention without placing limitations thereon.

BRIEF DESCRIPTION OF DRAWINGS

With the above and other related objects in view, the invention consists in the details of construction and combination of parts as will be more fully understood from the following description, when read in conjunction with the accompanying drawings in which.

DETAILED DESCRIPTION OF THE INVENTION

Figure 1:
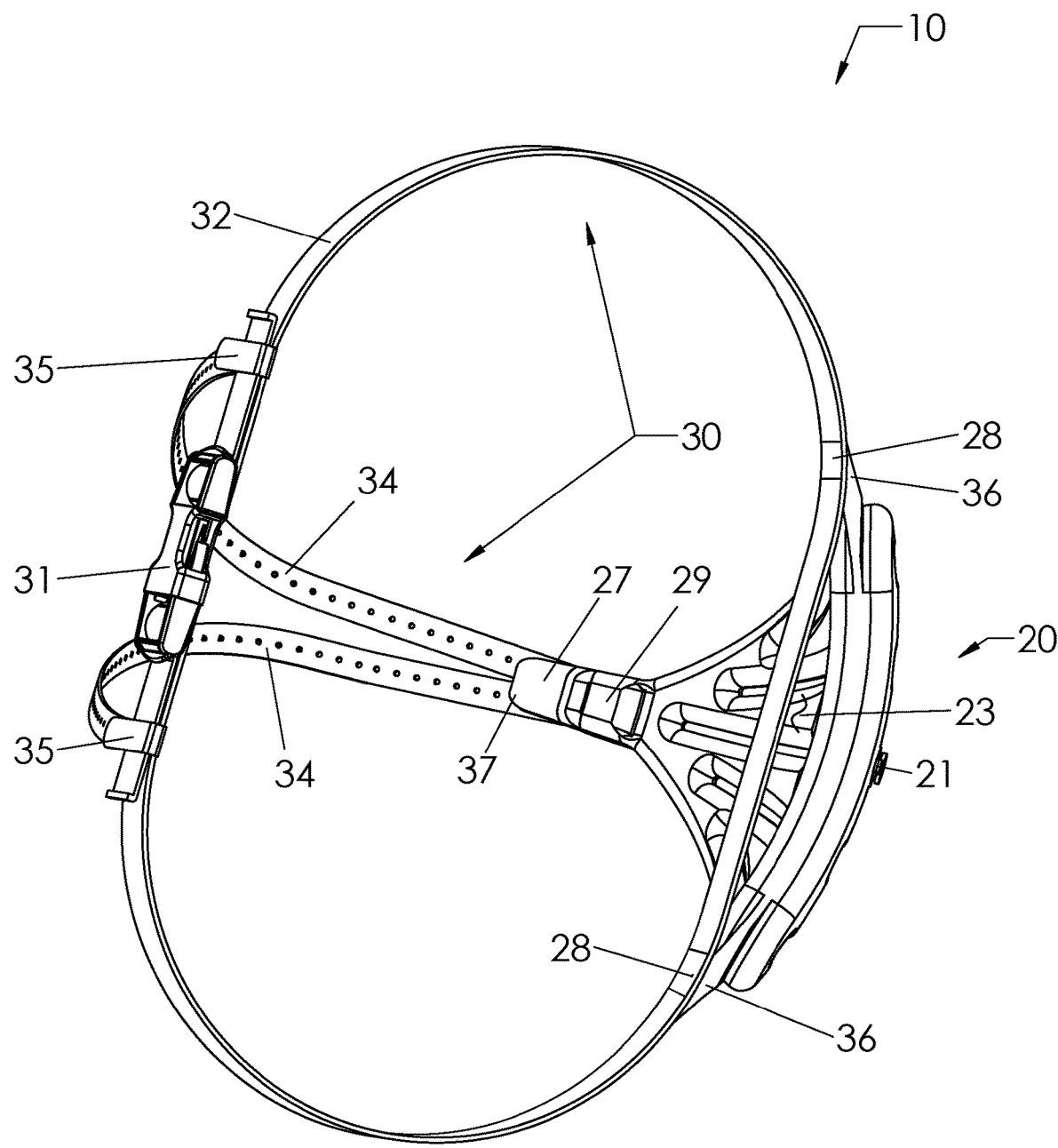
FIG. 1 represents a top-down view of a wearable device for treatments to enhance circulation in a lower torso.

Referring now to the drawings, the present invention is generally referred to with numeral 10. It can be observed that it is basically a wearable device for treatments to enhance circulation in a lower torso. Present invention 10 is unisex and comprises pouch assembly 20 and strap assembly 30.

Figure 2:
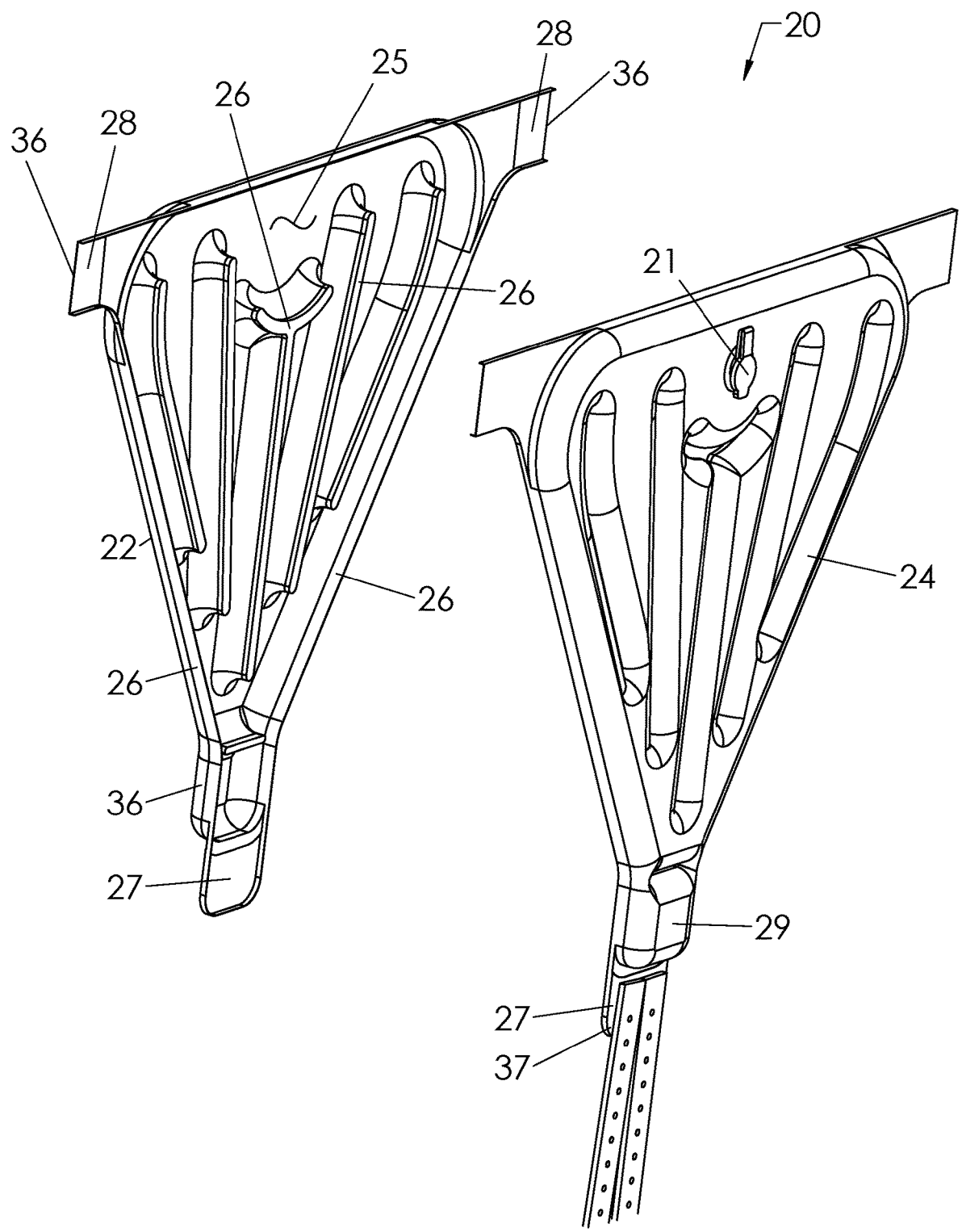
FIG. 2 is an isometric exploded view of a pouch assembly.

As seen in FIGS. 1 and 2, pouch assembly 20 comprises multiple layers and includes belt welds 28, lateral strap weld 27, inflation valve 21, and damming bubble 29. In a preferred embodiment, damming bubble 29 allows pouch assembly 20 to engorge by slowing warm water 42, seen in FIGS. 4A and 4B, exit at a bottom thereof to create overflow, otherwise it would flow-through present invention 10, rather than engorge. Pouch assembly 20 further comprises first layer 22 and second layer 24, that together define cavity 25. First layer 22 and second layer 24 have weld lines 26.

Figure 3:
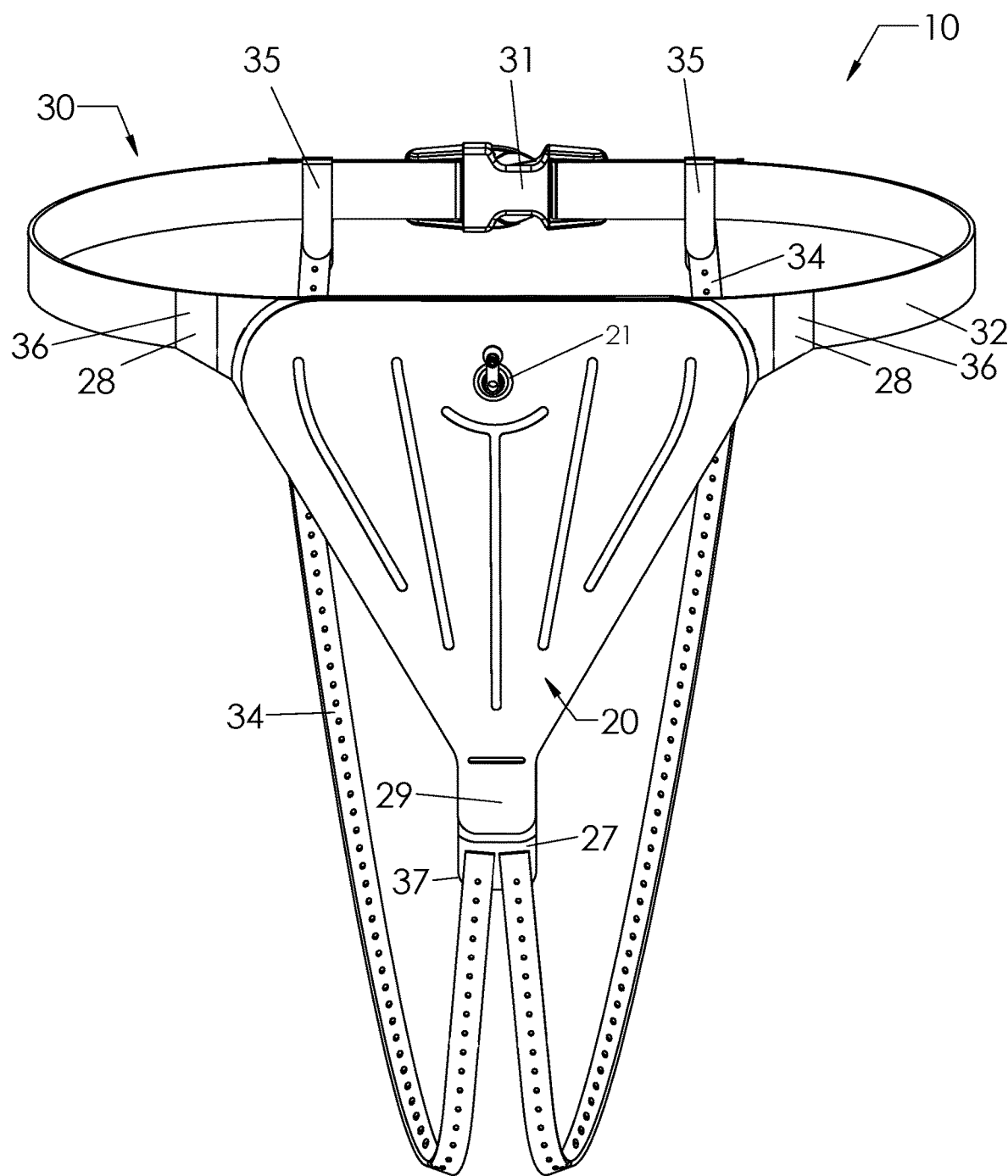
FIG. 3 is an angled-rear view of the wearable device for treatments to enhance circulation in the lower torso.

As seen in FIG. 3, strap assembly 30 consists of waist belt 32 and lateral straps 34. In a preferred embodiment, lateral straps 34 are perforated. Waist belt 32 is welded to belt welds 28, which are located at upper corners 36 of pouch assembly 20, which define a radius of pouch assembly 20. Waist belt 32 is joined by adjustable buckle 31. Lateral straps 34 are welded to lateral strap weld 27 located at lower corner 37 whereby both lateral straps 34 loop to attach to waist belt 32 by adjustable clips 35 and clip snaps 33, seen in FIG. 5B. Lateral straps 34 ensure a snug fit when secured to body 41, seen in FIGS. 4A and 4B, especially when in a standing position. Both strap assembly 30 and pouch assembly 20 are constructed from soft, yet durable materials.

Figure 4A:
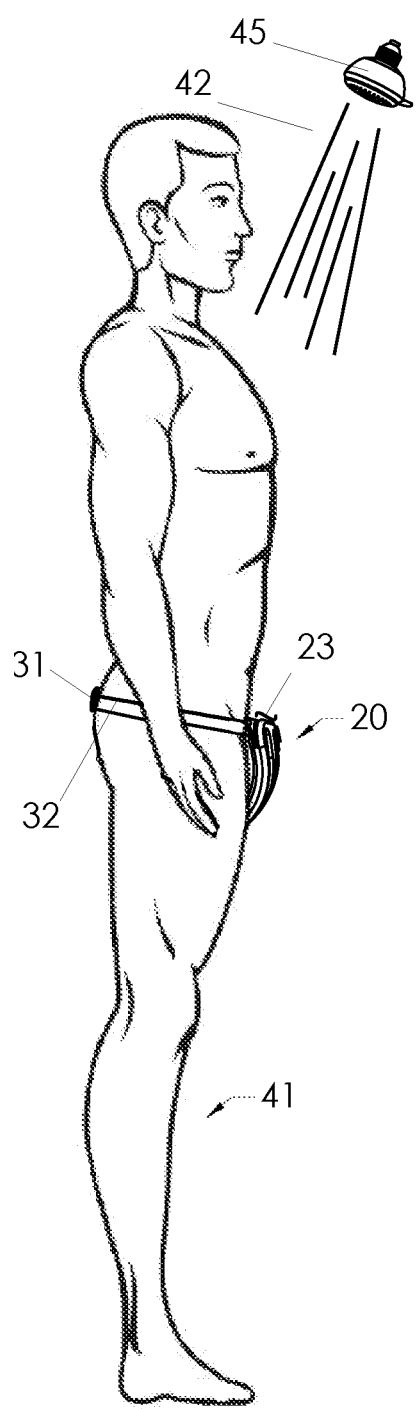
FIG. 4A is a side view of the wearable device for treatments to enhance circulation in lower torso being used in a frontal abdominal application.
Figure 4B:
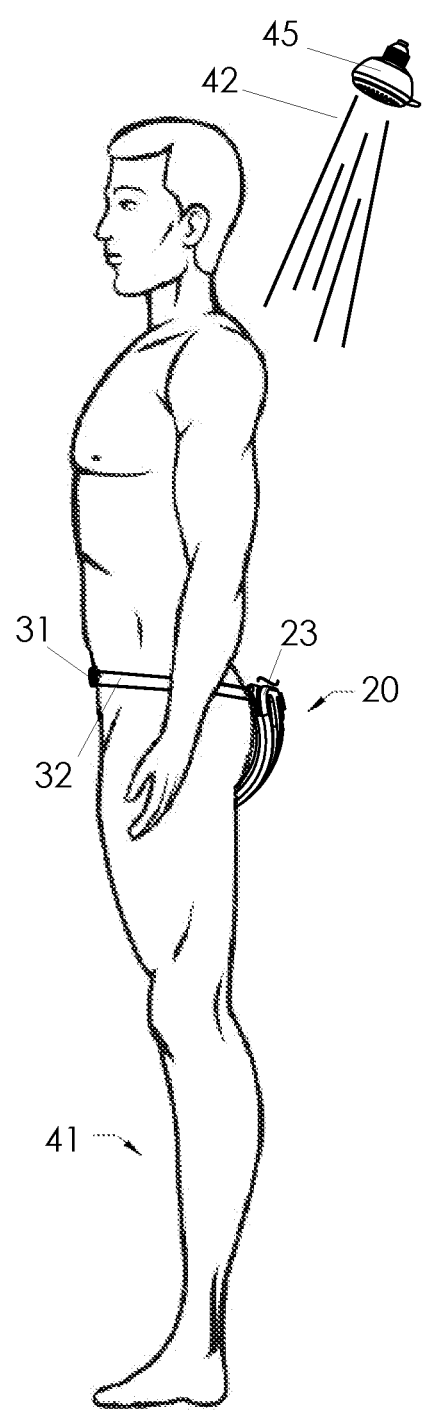
FIG. 4B is a side view of the wearable device for treatments to enhance circulation in lower torso being used in a rear abdominal application.

As seen in FIGS. 4A and 4B, this configuration creates a semi-sealed interface between pouch assembly 20, lateral straps 34, seen in FIG. 1, and body 41, forming pocket 23, which retains warm water 42 from water source 45 against body 41.

Figure 5A:
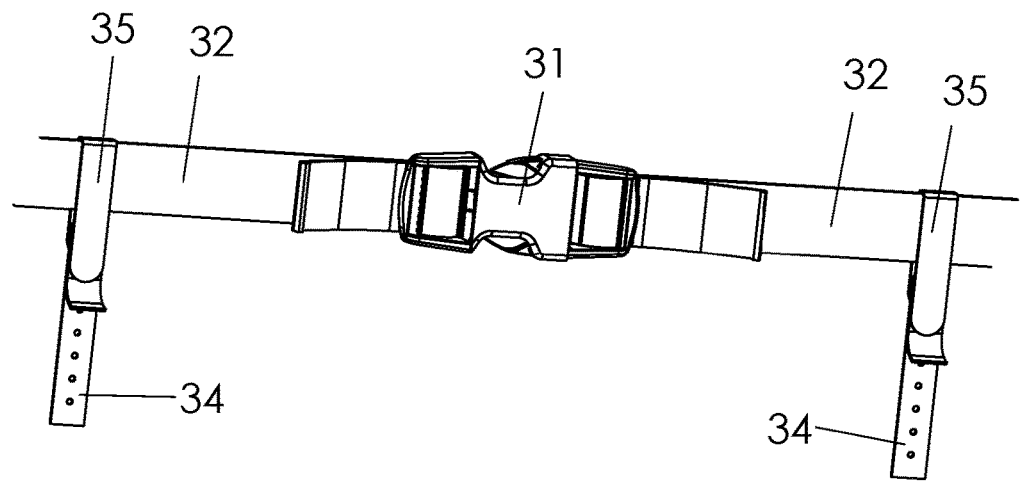
FIG. 5A is a front view of a strap assembly buckled.

As seen in FIG. 5A, adjustable buckle 31 is in a clipped configuration along with adjustable clips 35 looped around waist belt 32 and fastened in place, securing lateral straps 34 to waist belt 32.

Figure 5B:
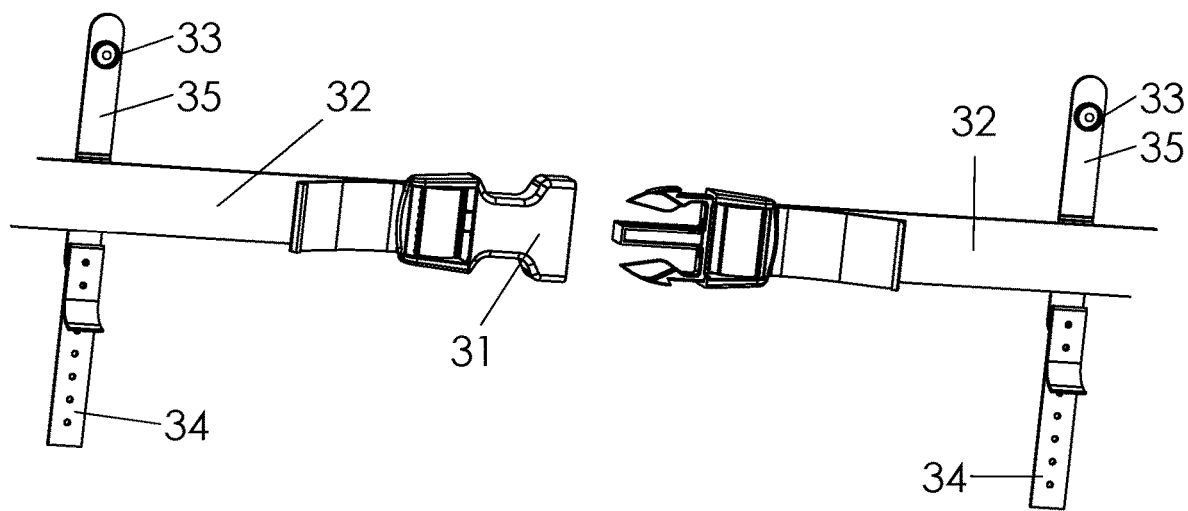
FIG. 5B is a front view of the strap assembly unbuckled.

As seen in FIG. 5B, adjustable buckle 31 is in an unclipped configuration along with adjustable clips 35 unfastened. Clip snaps 33 can be seen in this configuration, which are the mechanism in which adjustable clips 35 are fastened.

The materials used in strap assembly 30 and pouch assembly 20 are resistant to various elements such as temperature, water, suds, human biowaste, and pharmaceutical solutions. This design ensures the device's longevity and usability in various conditions. Strap assembly 30 is designed to provide secure fastening when the user is standing, contributing to its practicality, effectiveness in improving circulation in the lower torso and is put on and off easily with adjustable buckle 31 once strap assembly 30 has been adjusted for the user's body type.

In an ideal embodiment, present invention 10 is unisex and holds warm water 42, as seen in FIGS. 4A and 4B, in contact with wounds, enhancing circulation and increasing healing, thereby reducing the recovery period. Present invention 10 is unisex and reversible, allowing it to be worn on a front side or back side of body 41. The constant flow of warm water 42 from water source 45 allows the user to adjust the temperature and flow of water to the treatment area and provides longer periods of treatments. The constant flow of warm water 42 from water source 45 removes bacteria, germs, stool and urine from the treatment area. The open pocket design allows the user access to the treatment area during use. The continuous flow of water allows for the reliable replacement of clean, fresh water to the treatment area. Users do not need to heat water or carry water for use, making present invention 10 a safe treatment for users who struggle to transport water. Another benefit of a steadily replaced water source is that it is constantly replacing soiled water, cleaning, and it provides a steady temperature due to the constant water exchange. Present invention 10 has varying sizes, allowing for use with varying body types and sizes. Cavity 25 is inflatable, allowing adjustment of the fit.

In an ideal configuration, present invention 10 would be used in a standing position in a shower. As seen in FIGS. 4A and 4B, water source 45 provides a continuous source of warm water 42 that is easily regulated. Present invention 10 can be used in a frontal configuration, as seen in FIG. 4A. Present invention 10 can be used in a rear configuration, as seen in FIG. 4B.

Present invention 10 is washable and reusable. Present invention 10 encourages a non-sedimentary treatment technique, which can be applied in the user's daily routine of showering. Present invention 10 takes advantage of a large supply of hot water, providing prolonged use.

The foregoing description conveys the best understanding of the objectives and advantages of the present invention. Different embodiments may be made of the inventive concept of this invention. It is to be understood that all matter disclosed herein is to be interpreted merely as Illustrative, and not in a limiting sense.

What is claimed is:

1. A wearable device for treatments to enhance circulation in a lower torso comprising:
    A) a pouch assembly comprising first and second layers that define a cavity that is semi-sealed on all sides and is fillable; and
    B) a strap assembly, wherein said pouch assembly and said strap assembly define a pocket, said strap assembly comprises a waist belt and lateral straps, whereby said waist belt is secured at upper corners of said pouch assembly, said strap assembly further comprises adjustable clips that attach and detach said lateral straps from said waist belt, said strap assembly is configured to be secured around a body, whereby said strap assembly is configured to be secured around a front side or rear side of said body, said strap assembly comprises an adjustable buckle that attaches said waist belt to itself and adjusts a radius of said waist belt, said lateral straps are welded to a lateral strap weld located at a lower corner whereby both lateral straps loop to attach to said waist belt by said adjustable clips and clip snaps, whereby said lateral straps are joined at said lower corner and extend from said lower corner separately and attach to said waist belt apart a predetermined distance from each other, wherein a first of said lateral straps is attached by a first end of said adjustable buckle and a second of said lateral straps is attached by a second end of said adjustable buckle.

2. The wearable device for treatments to enhance circulation in the lower torso set forth in claim 1, further characterized in that when configured to be secured onto said body, said pouch assembly and said lateral straps define said pocket that is semi-sealed.

3. The wearable device for treatments to enhance circulation in the lower torso set forth in claim 1, further characterized in that when configured to be secured onto said body, said waist belt defines an opening to said pocket.

4. The wearable device for treatments to enhance circulation in the lower torso set forth in claim 1, further characterized in that said lateral straps are perforated.

5. The wearable device for treatments to enhance circulation in the lower torso set forth in claim 1, further characterized in that said pocket is configured to receive warm water.

6. The wearable device for treatments to enhance circulation in the lower torso set forth in claim 5, further characterized in that said pouch assembly holds said warm water when configured to be worn against said body.

7. The wearable device for treatments to enhance circulation in the lower torso set forth in claim 1, further characterized in that said strap assembly is secured around when configured to be worn against said body when standing.

8. The wearable device for treatments to enhance circulation in the lower torso set forth in claim 1, said adjustable clips can slide along said waist belt and be detached from said waist belt.

* * * * *